United States Patent
Tojo et al.

(10) Patent No.: US 10,111,580 B2
(45) Date of Patent: Oct. 30, 2018

(54) FIBER SENSOR

(71) Applicant: OLYMPUS CORPORATION, Tokyo (JP)

(72) Inventors: Ryo Tojo, Hachioji (JP); Hiromasa Fujita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/728,647

(22) Filed: Oct. 10, 2017

(65) Prior Publication Data

US 2018/0028055 A1 Feb. 1, 2018

Related U.S. Application Data

(63) Continuation of application No. PCT/JP2015/061277, filed on Apr. 10, 2015.

(51) Int. Cl.
*G02B 6/10* (2006.01)
*A61B 1/07* (2006.01)
(Continued)

(52) U.S. Cl.
CPC .............. *A61B 1/07* (2013.01); *A61B 1/005* (2013.01); *A61B 34/20* (2016.02); *A61B 2034/2061* (2016.02)

(58) Field of Classification Search
CPC ........... A61B 1/07; A61B 1/005; A61B 34/20; A61B 2034/2061
See application file for complete search history.

(56) References Cited

U.S. PATENT DOCUMENTS 5,132,529 A * 7/1992 Weiss .................. G01B 11/18
250/227.16
5,482,029 A * 1/1996 Sekiguchi .......... A61B 1/00039
600/109
(Continued)

FOREIGN PATENT DOCUMENTS

JP 2000-166854 A 6/2000
JP 2000-342514 A 12/2000
(Continued)

OTHER PUBLICATIONS

International Search Report dated Jun. 23, 2015 issued in PCT/JP2015/061277.
(Continued)

*Primary Examiner* — Ellen Kim
(74) *Attorney, Agent, or Firm* — Scully, Scott, Murphy & Presser, P.C.

(57) ABSTRACT

At least one optical fiber of a fiber sensor has sensing parts whose number is number of the anticipated inflection points+one or more, the anticipated inflection points being inflection points of a shape of a detection target range of a detection target. The number of the anticipated inflection points is decided based on one of a functional limit and a structural limit which limit a degree of freedom in a bending shape of the detection target. A space $L_1$ between the anticipated inflection points is $L_1 = r_1 \cdot \theta_1$, wherein $r_1$ is a curvature radius at a maximum bending of the detection target range of the detection target, $\theta_1$ is a central angle of an arc created by the space between the anticipated inflection points at the maximum bending, and $\theta_1 \geq \pi/2$.

16 Claims, 11 Drawing Sheets

(51) Int. Cl.
*A61B 1/005* (2006.01)
*A61B 34/20* (2016.01)

(56) References Cited

U.S. PATENT DOCUMENTS 6,127,672 A * 10/2000 Danisch ................. G01B 11/18
                                                                                   250/227.14
2016/0360951 A1* 12/2016 Hane ...................... G02B 23/26

FOREIGN PATENT DOCUMENTS

| JP | 2003-065735 A | 3/2003 |
| JP | 2007-130154 A | 5/2007 |
| JP | 2007-130175 A | 5/2007 |
| JP | 3920603 B2 | 5/2007 |
| JP | 2007-143600 A | 6/2007 |
| JP | 2011-200341 A | 10/2011 |
| JP | 2015-029831 A | 2/2015 |

OTHER PUBLICATIONS

English translation of International Preliminary Report on Patentability dated Oct. 19, 2017 together with the Written Opinion received in related International Application No. PCT/JP2015/061277.

* cited by examiner

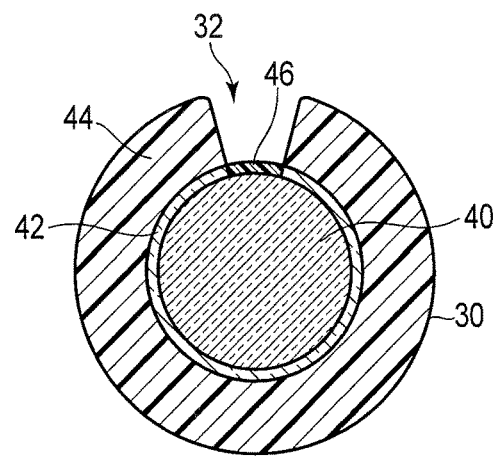
F I G. 2A
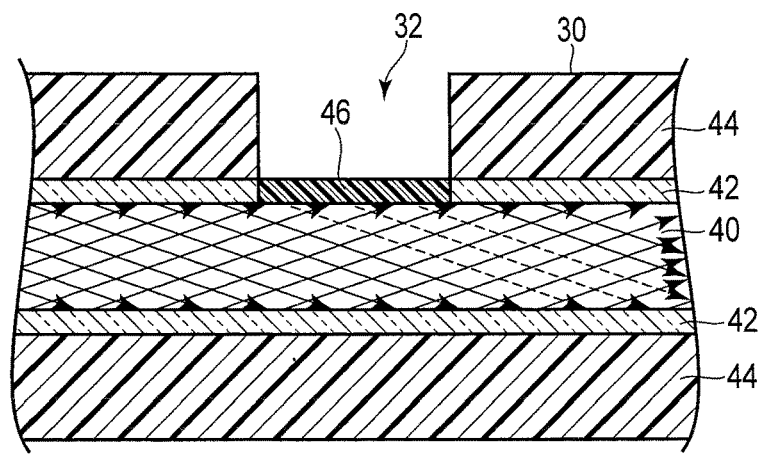
F I G. 2B
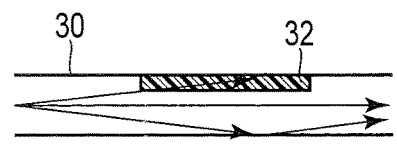
F I G. 3A

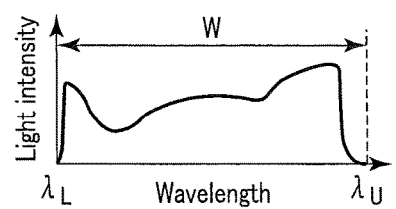
F I G. 4C
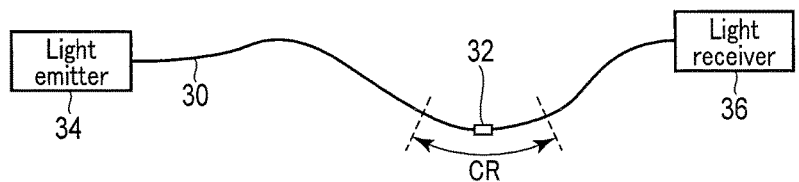
F I G. 5A
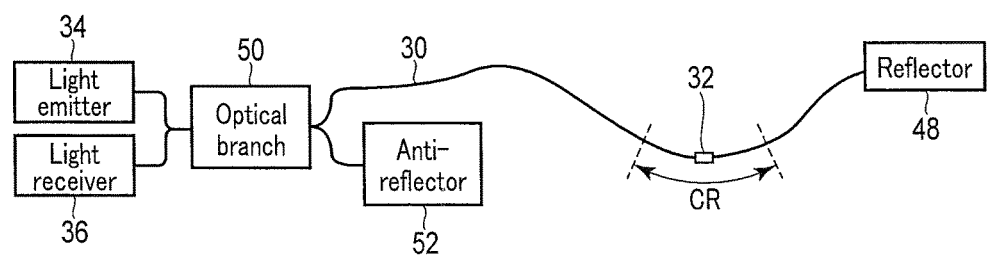
F I G. 5B

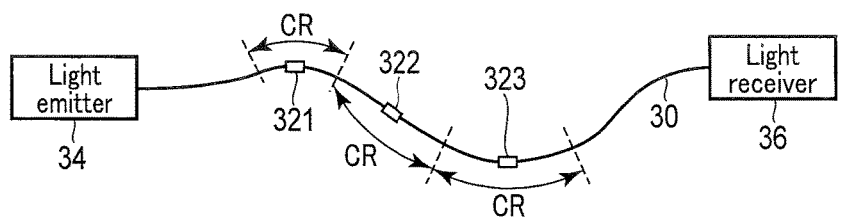
F I G. 6A
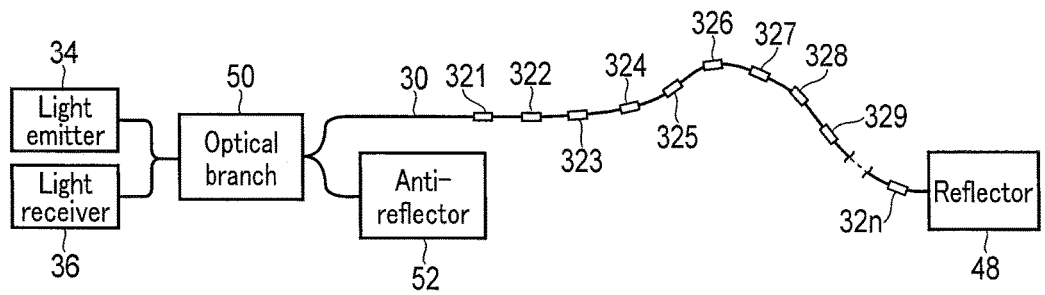
F I G. 6B
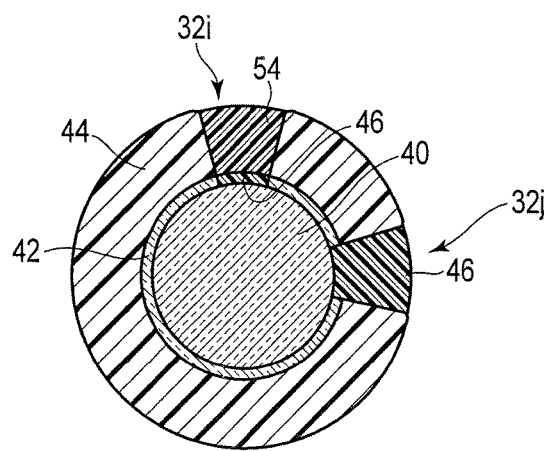
F I G. 7

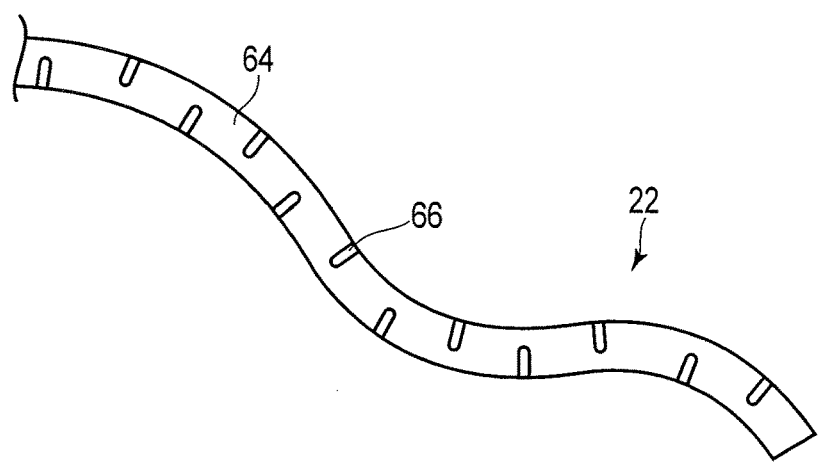
F I G. 10
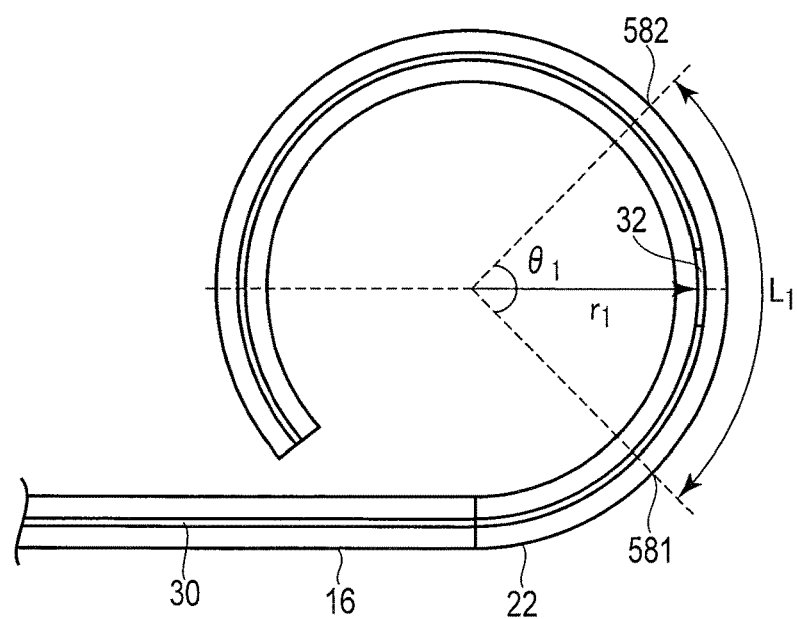
F I G. 11

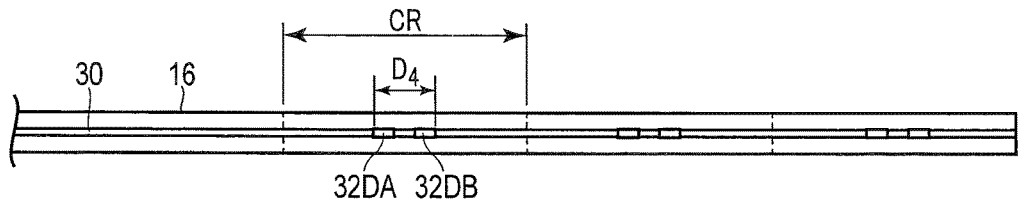
F I G. 18
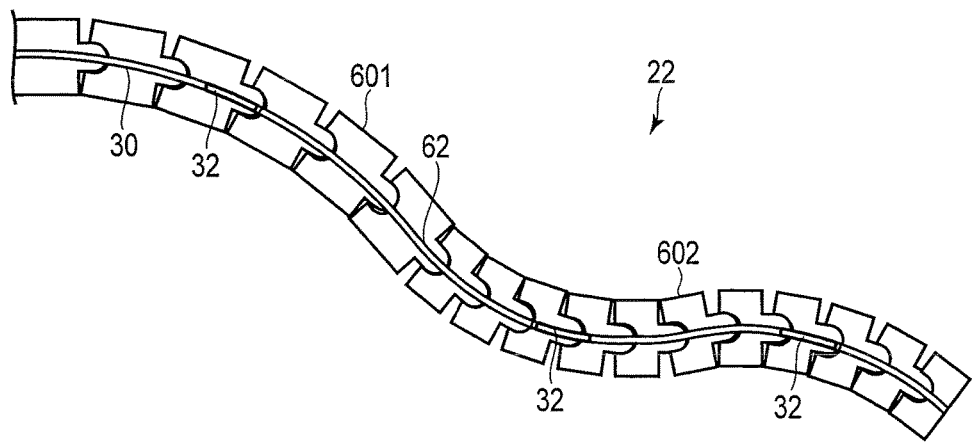
F I G. 19
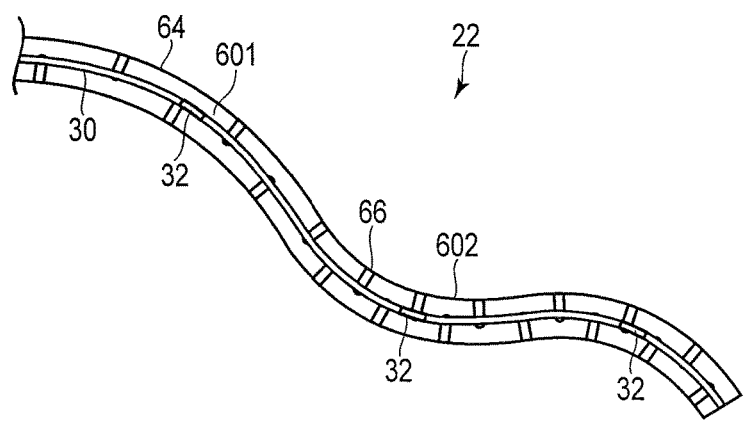
F I G. 20

US 10,111,580 B2

FIBER SENSOR

CROSS-REFERENCE TO RELATED APPLICATION

This application is a Continuation Application of PCT Application No. PCT/JP2015/061277, filed Apr. 10, 2015, the entire contents of which are incorporated herein by reference.

BACKGROUND OF THE INVENTION

1. Field of the Invention

The present invention relates to a fiber sensor.

2. Description of the Related Art

For example, Japanese Patent No. 3920603 discloses a flexible endoscope incorporating a fiber sensor. The fiber sensor is equipped with optical fibers each provided with sensing parts in an insertion section flexible tube of the endoscope, and detects a bending state of the insertion section flexible tube and then displays the bending state on a monitor screen. In the fiber sensor disclosed in this patent, the sensing parts are spaced out in an axial line direction of the insertion section flexible tube. Here, the space between the sensing parts is smaller in parts closer to the distal end of the insertion section flexible tube than in parts closer to the proximal end, so that the parts closer to the distal end that are bent with smaller curvature radii can be detected with a high degree of accuracy.

BRIEF SUMMARY OF THE INVENTION

According to an aspect of the present invention, there is provided a fiber sensor comprising at least one optical fiber having one or more sensing parts, a light emitter configured to cause light to enter the at least one optical fiber, and a light receiver configured to receive light emitted from the at least one optical fiber. The at least one optical fiber is laid in a detection target at least a part of which is bendable and is arranged along a longitudinal direction of the detection target in a detection target range which is the at least the part of the detection target. The fiber sensor is configured to detect light guided through the at least one optical fiber and thereby detect a state of the detection target range of the detection target. When anticipated inflection points are inflection points of a shape of the detection target range and are anticipated from one of a possible shape of the detection target range of the detection target and a state detectable in the detection target range, the at least one optical fiber has the sensing parts whose number is the number of the anticipated inflection points+one or more. The number of the anticipated inflection points is decided based on one of a functional limit and a structural limit which limit a degree of freedom in a bending shape of the detection target. A space $L_1$ between the anticipated inflection points is $$L_1 = r_1 \cdot \theta_1$$

wherein $r_1$ is a curvature radius at a maximum bending of the detection target range of the detection target, $\theta_1$ is a central angle of an arc created by the space between the anticipated inflection points at the maximum bending, and $\theta_1 \geq \pi/2$.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a sectional view showing an example of the configuration of a sensing part of the fiber sensor;

FIG. 2B is a sectional view of the sensing part along a longitudinal axis direction of the fiber sensor;

FIG. 3A is a diagram showing a case where an optical fiber is not bent, to illustrate a detection principle of the fiber sensor;

FIG. 4C is a graph showing one example of a spectrum of light exiting from the optical fiber;

FIG. 5A is a diagram illustrating the configuration of a transmission type fiber sensor;

FIG. 5B is a diagram illustrating the configuration of a reflection type fiber sensor;

FIG. 6A is a diagram illustrating the configuration of a transmission type fiber sensor comprising sensing parts;

FIG. 6B is a diagram illustrating the configuration of a reflection type fiber sensor comprising sensing parts;

FIG. 7 is a diametrical sectional view of the optical fiber showing another example of the configuration of a sensing part in the fiber sensor;

FIG. 10 is a diagram showing another example of the internal structure of the operation bending portion of the endoscope;

FIG. 11 is a diagram illustrating a third deciding method of the arrangement of the sensing parts of the fiber sensor in the operation bending portion of the endoscope;

FIG. 18 is a diagram illustrating another example of the arrangement of the sensing parts of the fiber sensor in the case where one sensing part is divided into two and then arranged;

FIG. 19 is a diagram showing one example of the internal structure of a bending portion of an endoscope to which a fiber sensor according to a second embodiment of the present invention is applied;

FIG. 20 is a diagram showing another example of the internal structure of the bending portion of the endoscope;

DETAILED DESCRIPTION OF THE INVENTION

Hereinafter, embodiments of the present invention will be described with reference to the drawings.

Although the present invention is applied to a medical flexible endoscope (e.g. an upper gastrointestinal endoscope, a large intestine endoscope, an ultrasonic endoscope, a cystoscope, a pyeloscope, or a bronchoscope) in examples described below, the present invention is not limited thereto. For example, the present invention is also applicable not only to the medical endoscope but also to a detecting apparatus, such as a catheter, a treatment instrument, or an industrial endoscope, which has an at least partly flexible insertion section to be inserted into a subject and which detects a bending amount of the insertion section. Further, the present invention is also applicable to a detecting apparatus which detects a bending amount, such as a detecting apparatus which is disposed in a structure to detect a bending amount of the structure. Additionally, the subject is not limited to a person, and may be an animal or some other structure. The present invention is available when an optical fiber having sensing parts is laid, in advance or according to need, in a detection target which is at least partly bendable, for example, when the optical fiber is inserted or disposed in the above subject or when the optical fiber is incorporated in or installed outside the detection target.

First Embodiment

Figure 1:
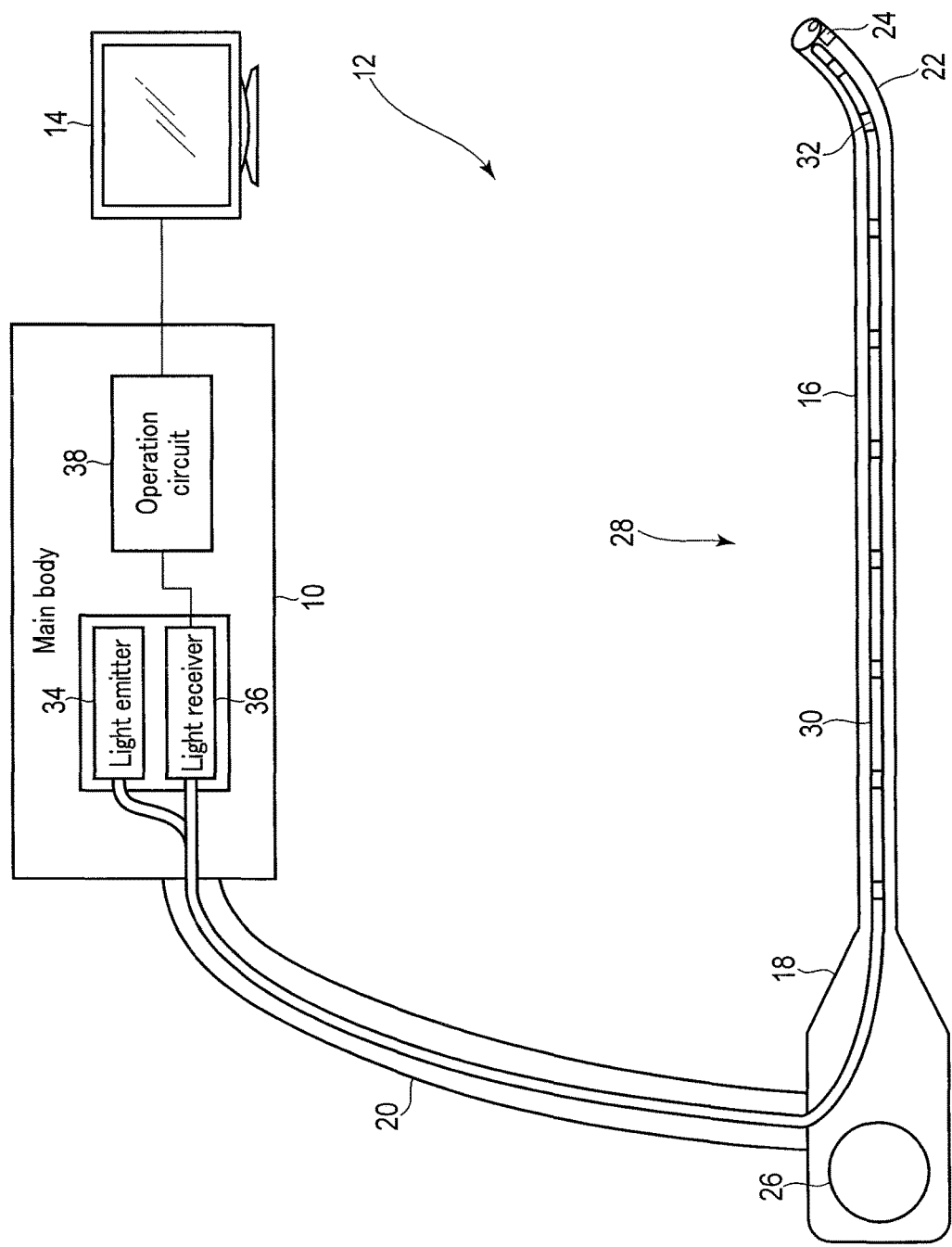
FIG. 1 is a diagram showing the overall configuration of an endoscope system incorporating a fiber sensor according to a first embodiment of the present invention.

As shown in FIG. 1, an endoscope system incorporating a fiber sensor according to a first embodiment of the present invention includes a main body 10, an endoscope 12 (i.e. the endoscope 12 means an endoscope which does not include the main body 10 in the present embodiment), and a display monitor 14. The endoscope 12 images an affected part, a lesion, or the like in a subject (e.g. a body cavity (lumen)) which is an observation target. The main body 10 subjects a result of imaging by the endoscope 12 to image processing. The display monitor 14 is connected to the main body 10, and displays an observation image which has been acquired by the endoscope 12 and subjected to image processing by the main body 10. The main body 10 is separate from the endoscope 12, and is a housing to which a connecting cable 20 of the endoscope 12 is connected.

The endoscope 12 is provided with an elongated insertion section 16 which is a bending member, an operation section 18 coupled to a proximal portion of the insertion section 16, and the connecting cable 20. The endoscope 12 is a tubular insertion device which inserts the tubular insertion section 16 into a body cavity. The insertion section 16 is inserted, for example, through the mouth, and the endoscope system observes the inside of the body.

The insertion section 16 includes a distal hard portion, an operation bending portion 22 which bends, and a flexible tubular portion, from the distal portion side to the proximal portion side of the insertion section 16. Here, a proximal portion of the distal hard portion is coupled to a distal portion of the operation bending portion 22, and a proximal portion of the operation bending portion 22 is coupled to a distal portion of the flexible tubular portion.

The distal hard portion is a distal portion of the insertion section 16 and a distal portion of the endoscope 12, and is a hard member. An imaging device 24 is provided in this distal hard portion.

The operation bending portion 22 bends in a desired direction in response to an operation by an endoscope operator (a worker such as a doctor) of a bending operation knob 26 provided in the operation section 18. The operator bends the operation bending portion 22 by operating the bending operation knob 26. The position and direction of the distal hard portion are changed by the bending of the operation bending portion 22, and the observation target is caught in an observation field of view which is an imaging range for the imaging device 24. Illumination light is applied to the observation target which has been caught as above from an unshown illumination window provided in the distal hard portion, and the observation target is illuminated accordingly. The operation bending portion 22 is composed of unshown node rings linked along a longitudinal direction of the insertion section 16. The operation bending portion 22 bends by relative turning of the node rings.

The flexible tubular portion has desired flexibility, and is bent by external force. The flexible tubular portion is a tubular member extending from the operation section 18.

The connecting cable 20 connects the operation section 18 and the main body 10 to each other.

Furthermore, the endoscope system has a fiber sensor 28 according to the present embodiment which detects a bending state (bending amount) in parts within a predetermined range (detection target range) of the insertion section 16 that is a detection target including the operation bending portion 22.

The fiber sensor 28 includes an optical fiber 30 having sensing parts 32 arranged along the longitudinal direction of the insertion section 16 within the detection target range, a light emitter 34, and a light receiver 36. The optical fiber 30 is inserted through the insertion section 16 from the main body 10 via the inside of the connecting cable 20 and the inside of the operation section 18, and is thereby laid in the insertion section 16 which is the at least partly bendable detection target.

The light emitter 34 includes, for example, a light source such as an LED, and causes light to enter the optical fiber 30. The light receiver 36 includes, for example, a light receiving element, and receives the light emitted from the optical fiber 30 and outputs a light receiving signal corresponding to the intensity of the received light or the like.

Here, if the optical fiber 30 bends in accordance with the bending of the insertion section 16, the sensing parts 32 emit the light guided through the optical fiber 30 toward the outside of the optical fiber 30 or absorb the light in accordance with the bending shape of the optical fiber 30. The amount of light emitted toward the outside of the optical fiber 30 or absorbed corresponds to the bending amount of the optical fiber 30. The sensing parts 32 are processed so that the amount of light corresponding to the bending amount of the optical fiber 30 is leaked to the outside of the optical fiber 30 or absorbed. In other words, the sensing parts 32 change optical characteristics such as the amount of the light guided by the optical fiber 30 in accordance with the bending amount of the insertion section 16 (an optical characteristics changing portion). The sensing parts 32 are provided within at least the detection target range of the insertion section 16 which is a place where bending is to be detected or which is located in the vicinity of this place.

Therefore, the intensity of light received by the light receiver 36 corresponds to the magnitude of the bending (bending amount) of the insertion section 16, so that the light receiving signal output by the light receiver 36 is information indicating the bending amount of the insertion section 16. Thus, the light receiver 36 functions as a state detector which detects the state of the insertion section 16 that is the detection target within the detection target range.

The main body 10 further has an operation circuit 38 which converts the bending amount detected by the fiber sensor 28 into a shape, and can display, on the display monitor 14, the shape of the insertion section 16 obtained by the conversion within the predetermined range (detection target range).

Here, the sensing parts 32 provided in the optical fiber 30 are described.

As shown in FIG. 2A and FIG. 2B, the optical fiber 30 comprises a core 40 which is present in the center and which guides light, a cladding 42 which is provided around the core 40 and which stably confines light into the core 40, and a jacket 44 which protects the core 40 and the cladding 42 from physical shock and thermal shock.

The sensing part 32 is obtained by removing the jacket 44 and the cladding 42 to expose a part of the core 40 at a predetermined position of the optical fiber 30 in a longitudinal axis direction, and forming a light absorber 46 to produce an absorption wavelength characteristics region in the exposed part of the core 40. The light absorber 46 is formed substantially at about the thickness of the cladding. The jacket 44 and the cladding 42 are removed by laser processing or by use of, for example, a photographic processing and an etching process. In this instance, if the core 40 is microscopically damaged, the core 40 leaks light, loses light to be guided, or becomes vulnerable to bending, so that it is desirable to process the core 40 in a least damaging way.

In such a sensing part 32, if the optical fiber 30 bends, a slight amount of light transmitted through the optical fiber 30 leaks into the sensing part 32 accordingly. That is, the sensing part 32 is provided on one side of the optical fiber 30, and the amount of the leaked light (only a slight amount of leaked light) changes in accordance with the bending of the optical fiber 30. That is, the sensing part 32 changes the optical characteristics, for example, light transmission amount of the optical fiber 30.

Figure 3B:
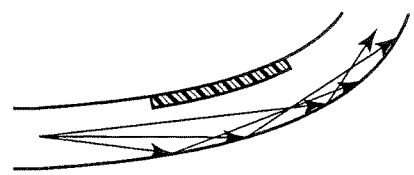
FIG. 3B is a diagram showing a case where the optical fiber is bent in an upward direction on the paper surface, to illustrate the detection principle of the fiber sensor.
Figure 3C:
FIG. 3C is a diagram showing a case where the optical fiber is bent in a downward direction on the paper surface, to illustrate the detection principle of the fiber sensor.

FIG. 3A, FIG. 3B, and FIG. 3C show schematic diagrams of the light transmission amounts corresponding to the bending of the optical fiber 30. Here, FIG. 3A shows the light transmission amount in the case where the optical fiber 30 is not bent, FIG. 3B shows the light transmission amount in the case where the optical fiber 30 is bent to the side on which the sensing part 32 is provided, and FIG. 3C shows the light transmission amount in the case where the optical fiber 30 is bent to the side opposite to the side on which the sensing part 32 is provided. As shown in FIG. 3A, FIG. 3B, and FIG. 3C, these cases are ranked in descending order of light transmission amount: the case where the optical fiber 30 is bent to the side on which the sensing part 32 is provided, the case where the optical fiber 30 is not bent, and the case where the optical fiber 30 is bent to the side opposite to the side on which the sensing part 32 is provided. It is therefore possible to detect the bending amount in the sensing part 32 by measuring the intensity of the light emitted from the optical fiber 30. Moreover, the diametrical position in the optical fiber 30 where the sensing part 32 is provided, that is, the direction of the sensing part 32 is known, so that a bending direction can also be known, and the operation circuit 38 can calculate the bending shape of the insertion section 16 which is the detection target for the fiber sensor 28 by the bending direction and the bending amount.

The light from the light emitter 34 is partly absorbed when falling on the light absorber 46, and the remaining light returns to the core 40. This is clearly imaged in FIG. 2B. Full-line arrows indicate the light supplied from the light emitter 34. The light falling on the sensing parts 32 is partly absorbed, and the rest is returned to the core 40 as dotted-line arrows.

It is therefore possible to detect the change of the bending amount in the part of the sensing part 32 by measuring the intensity of the light which has passed through the light absorber 46 of the sensing parts 32.

Thus, the fiber sensor 28 comprises the light emitter 34 which causes light to enter the optical fiber 30, and the light receiver 36 which detects the light emitted from the optical fiber 30. Here, there are two types of configurations of the fiber sensor 28: a transmission type and a reflection type.

As shown in FIG. 5A, the transmission type is configured to supply light to the optical fiber 30 from the light emitter 34 disposed at one end of the optical fiber 30, provide an optical effect to the light guided through the optical fiber 30 by the light absorber 46 of the sensing part 32 located partway on the optical fiber 30, and receive the light transmitted through the optical fiber 30 by the light receiver 36 disposed at the other end of the optical fiber 30. Thus, the transmission type has the light emitter 34 and the light receiver 36 distributed and arranged on both sides of the optical fiber 30. When this transmission type is adopted, it is only necessary to fold back the optical fiber 30 in the distal hard portion of the insertion section 16, and insert the optical fiber 30 through the insertion section 16. In addition, the bending amount found from the light intensity detected by the light receiver 36 not only relates to the part where the sensing part 32 is provided but also relates to a predetermined range of length (a later-described shape calculation range CR) including the sensing part 32.

In contrast, as shown in FIG. 5B, the reflection type is configured to have the light emitter 34 and the light receiver 36 arranged on the same side of the optical fiber 30, and has a reflector 48 provided at the other end of the optical fiber 30, so that light entering from one end of the optical fiber 30 is reflected by the reflector 48 and then emitted from the one end of the optical fiber 30. Thus, the light emitter 34, the light receiver 36, and the one end of the optical fiber 30 are optically connected via an optical branch 50. This optical branch 50 includes an optical distributor (optical coupler), a half mirror, a beam splitter, or the like, but here, is an optical branch having 2×2 ports. An anti-reflector 52 is optically connected to the remaining port to which the light emitter 34, the light receiver 36, and the optical fiber 30 are not optically connected. Additionally, the aforementioned reflector 48 is, for example, a mirror formed by depositing aluminum or the like over an optical fiber. That is, the reflector 48 returns, to the side of the light receiver 36, the light which is supplied from the light emitter 34 and then reaches the end of the optical fiber 30 through the sensing part 32.

Therefore, in this reflection type fiber sensor 28, the light from the light emitter 34 is branched by the optical branch 50 and then enters the one end of the optical fiber 30 and the anti-reflector 52. The light supplied and then guided by the optical fiber 30 is provided with the optical effect by the light absorber 46 of the sensing part 32 located partway on the optical fiber 30, and reflected by the reflector 48 at the other end of the optical fiber 30. This reflected light becomes return light which is guided through the optical fiber 30 in the opposite direction, is again provided with the optical effect by the light absorber 46 of the sensing parts 32, and exits from the one end of the optical fiber 30. The return light exiting from the optical fiber enters the optical branch 50, is branched by the optical branch 50, and then enters the light emitter 34 and the light receiver 36. Then the light receiver 36 detects the intensity of the return light which has entered. An output signal of this light receiver 36 is sent to the operation circuit 38.

In addition, the other of the return light from the optical fiber 30 which is branched by the optical branch 50 and then enters the light emitter 34 does not affect the light emitter 34, and is neglected. Moreover, the other of the light from the light emitter 34 which is branched by the optical branch 50 enters the anti-reflector 52, and therefore does not enter the light receiver 36, and does not effect the detection by the light receiver 36. In addition, a light source monitor may be provided instead of the anti-reflector 52. This light source monitor detects the light from the light emitter 34 which is branched and then enters the light source monitor, thereby enabling feedback control of the amount of light emission by the light emitter 34. Naturally, it is preferable to provide both the light source monitor and the anti-reflector 52 to prevent the light which does not enter this light source monitor from being reflected and affecting the light receiver 36.

As described above, it is possible to detect the states of more than one range by using more than one optical fiber 30 which is provided with one sensing part 32, and arranging the sensing parts 32 at different positions in the longitudinal direction of the insertion section 16.

Furthermore, the number of sensing parts 32 in one optical fiber 30 can be more than one. FIG. 6A shows the transmission type fiber sensor 28 having three sensing parts: a first sensing part 321, a second sensing part 322, and a third sensing part 323. FIG. 6B shows the reflection type fiber sensor 28 having n sensing parts: first to n-th sensing parts 321 to 32n.

Here, when more than one sensing part 32 are provided, not only the sensing parts 32 are arranged along the longitudinal axis of the optical fiber 30 as shown in FIG. 6A and FIG. 6B, but also another sensing part (j-th sensing part 32j) may be provided for one sensing part (i-th sensing part 32i) at substantially the same place on the longitudinal axis in an orthogonal direction or in a direction which is diametrically axially different as shown in FIG. 7. In this structure, it is possible to not only detect the bending amount within a measurement range corresponding to the sensing parts but also detect the direction of bending.

In each sensing part, the light absorber 46 may remain bare as shown in FIG. 2A and FIG. 2B, but the part on the light absorber 46 where the jacket 44 and the cladding 42 are removed may be filled with a jacket-like member as a sensing part protector 54 to recover the original shape of the optical fiber 30 as in the i-th sensing part 32i shown in FIG. 7. Alternatively, as in the j-th sensing part 32j shown in FIG. 7, the light absorber 46 may be formed to fill the part where the jacket 44 and the cladding 42 are removed to recover the original shape of the optical fiber 30.

Figure 4A:
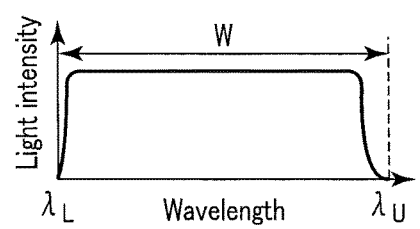
FIG. 4A is a graph showing one example of a spectrum of light entering the optical fiber.
Figure 4B:
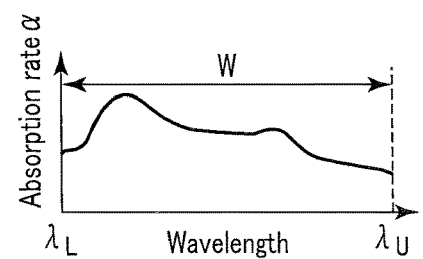
FIG. 4B is a graph showing one example of an absorption spectrum of a light absorber provided in the sensing part.

When the number of sensing parts 32 in one optical fiber 30 is more than one, for example, a material having an absorption spectrum shown in FIG. 4B for the light from an ideal light source having a substantially uniform optical spectrum within wavelength bands $\lambda_L$ to $\lambda_U$ shown in FIG. 4A is used for the light absorber 46 provided in the sensing part 32 of the optical fiber 30. Here, W is an emission wavelength region of the ideal light source. When fallen on the light absorber 46, light from the ideal light source is absorbed at the ratio of the aforementioned absorption spectrum, and the remaining light is returned to the core 40.

The substantially uniform light supplied from the light emitter 34 change to light having a spectrum provided with an optical effect by the absorption spectrum of the sensing parts 32, such as a spectrum shown in FIG. 4C.

The light absorber 46 used in each of the sensing parts 32 has a different absorption spectrum. Moreover, the optical effect by each of the sensing parts 32 is separately detected, so that when more than one sensing parts 32, for example, n sensing parts 32 including the first to n-th sensing parts 321 to 32n shown in FIG. 6B are formed in the optical fiber 30, the bending amount and the bending direction in the measurement range corresponding to each of the sensing parts 32 can be detected.

In addition, a technique other than the one using the light absorber 46 described above may be used for the configuration which provides an optical effect in the sensing parts 32. Moreover, a combination of the light absorber 46 described above and the other technique may be used. The use of this combination makes it possible to further increase the number of sensing parts 32. That is, the sensing parts 32 are not limited to ones that change the light transmission amount which is the optical characteristics of the optical fiber 30, and may be ones that change the state of light including a spectrum or a polarized wave. Moreover, the light receiver 36 has only to detect the light intensity, for example, the optical characteristics corresponding to the state of light including a spectrum or a polarized wave as described above.

For example, a light emitting element such as a fluorescent member can be formed in the sensing part 32 instead of the light absorber 46 described above. The fluorescent member has characteristics that absorb short-wavelength-side light and generate light on a long wavelength side. In the case of such a fluorescent member, the light conversion method is different from that of the light absorber 46 described above, so that the light falling on the sensing part 32 is absorbed, and the sensing part 32 generates scattered light. The amount of this light generation changes in accordance with the bending direction and the bending amount because the amount of light falling on the fluorescent member increases or decreases depending on the amount of bending. When such a fluorescent member is used, detection sensitivity is slightly lower in many cases than when the light absorber 46 described above is used.

Furthermore, a laminated dielectric film may be provided instead of the light absorber 46 described above. The laminated dielectric film has characteristics that lose a certain spectrum to the outside of the optical fiber due to the incident angle of light, that is, the bending of the optical fiber. It is preferable to further form a dielectric film effect increasing resin on the laminated dielectric film.

Now, deciding methods of the number of sensing parts 32 of the fiber sensor 28 are described with reference to FIG. 8.

The fiber sensor 28 uses more than one optical fiber 30 which is provided with one sensing part 32, or uses one optical fiber 30 provided with more than one sensing part 32, or combines these cases and uses more than one optical fiber 30 which is provided with more than one sensing part 32. In each case, more than one sensing part 32 are arranged within a detection target range DR of the insertion section 16 and at different positions along the longitudinal direction of the insertion section 16, whereby it is possible to detect more than one state, that is, bending amount in the detection target range DR of the insertion section 16, and calculate the shape of this part. In FIG. 8, the reference number 56D indicates the distal end of the detection target range DR, and the reference number 56P indicates the proximal end of the detection target range DR.

Furthermore, in the present embodiment, if inflection points (points where the bending direction changes) of the shape of the insertion section 16 that are anticipated to be generated in the actual use in which the shape detection is conducted are referred to anticipated inflection points, the number of sensing parts 32 provided in the detection target range DR is the number of the anticipated inflection points+ one or more.

Here, the anticipated inflection points are points at both ends of a range in which a little change of the bending amount can be expected in the shape of the insertion section 16 in the actual use. That is, in the range (later-described shape calculation range CR) intervening between the anticipated inflection points (a first anticipated inflection point 581 and a second anticipated inflection point 582) adjacent in the longitudinal direction of the insertion section 16, one sensing part 32 can highly accurately detect the bending amount. In contrast, in ranges beyond the anticipated inflection points, there is a stronger possibility of a great change of the bending amount, and highly accurate detection of the bending amount is no longer possible by one sensing part 32.

In addition, the bending amount can also be said to be an average curvature of this shape calculation range CR. Thus, the curvature and the bending amount are different in the strict sense, but can be considered substantially equivalent as far as the detection value of the fiber sensor 28 is concerned.

Furthermore, the anticipated inflection points anticipate spaces produced from the structure and hardness of the insertion section 16, that is, the number of the anticipated inflection points. Specifically, one or more of the first to fourth deciding methods described below is selected, the space between the inflection points are anticipated, and the number of the anticipated inflection points is decided.

Initially, the first deciding method is described.

Figure 9:
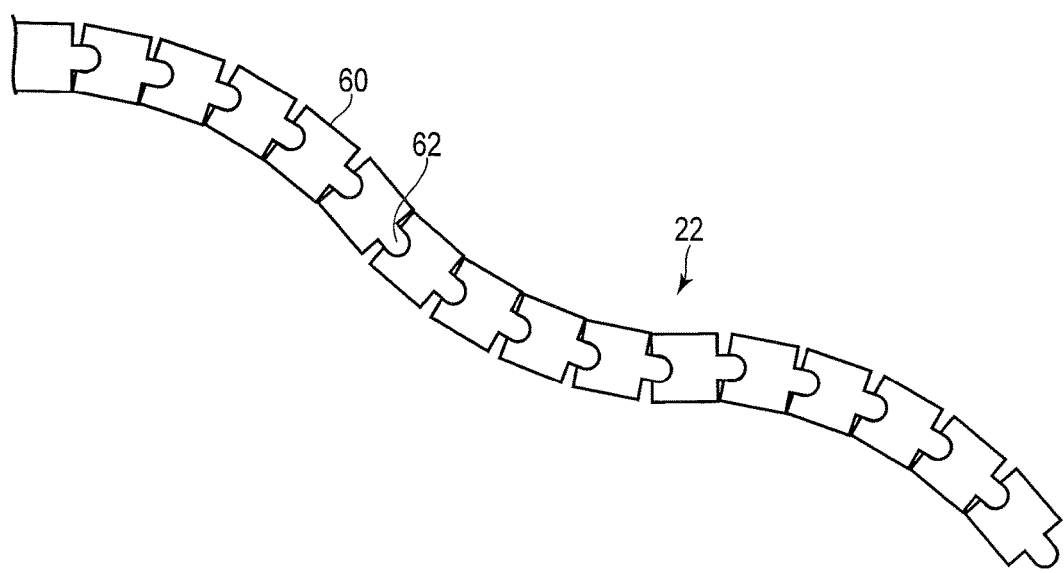
FIG. 9 is a diagram showing one example of the internal structure of an operation bending portion of an endoscope to which the fiber sensor according to the first embodiment is applied.

As described above, the operation bending portion 22 is composed of the node rings linked along the longitudinal direction of the insertion section 16. Specifically, as shown in FIG. 9, cylindrical rigid members 60 which are the node rings are linked by bending mechanisms 62. The bending mechanisms 62 link the rigid members 60 by, for example, rivets so that the anterior and posterior rigid members 60 can turn. FIG. 9 shows an example of the structure of the operation bending portion 22 capable of bending on one plane for the simplification of explanation. For example, a combinational structure in which the bending mechanisms 62 are provided to be 90 degrees rotated around an axis along an insertion direction makes it possible to configure the operation bending portion 22 capable of bending in any direction with regard to the insertion direction.

When the structure of the operation bending portion 22 comprises the rigid members 60 and the bending mechanisms 62 as above, the space between the inflection points is equal to or more than ten times the rigid member 60, and the number of the anticipated inflection points is decided accordingly.

Consequently, it is possible to decide the number of the anticipated inflection points in the case where the structure of the operation bending portion 22 comprises the rigid members 60 and the bending mechanisms 62, and the bending amount can be accurately detected by a small number of sensing parts 32.

FIG. 10 shows the internal structure of the operation bending portion 22 different from that in FIG. 9. In this structure of the operation bending portion 22, slits 66 are provided in a long and rigid cylindrical member 64. In addition, FIG. 10 shows an example of the structure of the operation bending portion 22 capable of bending on one plane for the simplification of explanation, in the same manner as FIG. 9. For example, a combinational structure in which the slits 66 are provided to be 90 degrees rotated around an axis along the insertion direction makes it possible to configure the operation bending portion 22 capable of bending in any direction with regard to the insertion direction.

When the operation bending portion 22 has such a structure, the slits 66 are considered as the bending mechanisms 62, and the ranges in which the slits 66 of the cylindrical member 64 are not present are considered as the rigid members 60, so that the space between the inflection points is equal to or more than ten times the rigid member 60, and the number of the anticipated inflection points is decided accordingly.

In addition, when the slits 66 are small in width, the range between the centers of the widths of the slits 66 adjacent in the longitudinal direction of the operation bending portion 22 can be used as the range in which the slits 66 are not present.

Next, the second deciding method is described.

Bendability of the insertion section 16 is generally related with the diameter $\phi$ of the insertion section 16, and the insertion section 16 is easily bent when the diameter $\phi$ is large, and the insertion section 16 is not easily bent when the diameter $\phi$ is small. Thus, as shown in FIG. 8, the space between the inflection points is equal to or more than ten times the diameter $\phi$ of the insertion section 16, and the number of the anticipated inflection points is decided accordingly.

Consequently, it is possible to decide the number of the anticipated inflection points on the basis of the diameter $\phi$ of the insertion section 16, that is, the bendability of the insertion section 16, and the bending amount can be accurately detected by a small number of sensing parts 32.

Next, the third deciding method is described.

The operation bending portion 22 can be bent by the operation of the bending operation knob 26 provided in the operation section 18. In general, the shape of the operation bending portion 22 by the operation is nearly an arc shape, as shown in FIG. 11. That is, there is a little change in the bending amount of the operation bending portion 22 in the longitudinal direction. Therefore, the bending amount can be detected even by one sensing part 32. On the other hand, there are cases where the operation bending portion 22 is bent by external force, and the bending amount considerably changes in the longitudinal direction of the operation bending portion 22. In such cases as well, there is a little change in the bending amount due to the structure of the operation bending portion 22 within a certain range in the longitudinal direction. Accordingly, the range in which there is a little change in the bending amount is found by Equation (1) below to decide the number of the anticipated inflection points for the shape in the case where external force is applied.

The operation bending portion 22 is also limited in the bending amount due to structural limits. The number of the anticipated inflection points is decided so that a space $L_1$ between the inflection points of the operation bending portion 22 satisfy Equation (1) below:

$$L_1 = r_1 \cdot \theta_1 \quad (1)$$

wherein $r_1$ is a curvature radius when the operation bending portion 22 is bent to the maximum, $\theta_1$ is a central angle, and $\theta_1 \geq \pi/2$.

Thus, the number of the anticipated inflection points can be decided from the maximum bending amount, that is, minimum curvature radius of the operation bending portion 22, and the bending amount can be accurately detected by a small number of sensing parts 32.

In addition, when the operation bending portion 22 has a mechanism which varies in hardness, the curvature radius $r_1$ has a value at which the hardness is set to the minimum.

The first to third deciding methods of the number of the anticipated inflection points described above decide the upper limits such that the number of sensing parts 32 may not be unnecessarily great.

In addition, the first to third deciding methods described above is not exclusively applied to the operation bending portion 22, and may also be applied to any range of the insertion section 16.

Moreover, the first to third deciding methods described above decide the number of the anticipated inflection points from the structure or hardness of the insertion section 16, but may further decide on the basis of, for example, the structure or hardness of the subject. For example, if the operator performs an operation of pressing the operation bending portion 22 to, for example, the lining in the subject, the operation bending portion 22 bends beyond the maximum bending amount of the operation bending portion 22 by the bending operation knob 26 due to the press force. In this case as well, how much force is applied can be anticipated by what the subject is, so that the value of the maximum bending amount can be decided in advance, and the number of the anticipated inflection points can be decided by the third deciding method described above.

Next, the fourth deciding method is described.

Figure 12:
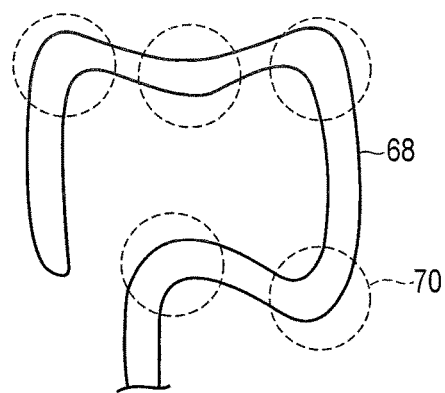
FIG. 12 is a diagram showing a schematic shape of a large intestine as one example of a subject.

When the insertion section 16 is inserted into a subject having a certain fixed shape such as the shape of the large intestine, the number of the anticipated inflection points may be decided on the basis of this shape. For example, as shown in FIG. 12, a large intestine 68 has five parts 70 in which the bending amount is great, so that the number of the anticipated inflection points is also five.

As a result, the number of the anticipated inflection points may be decided on the basis of the shape that is the same as or close to the shape by which a state is actually detected, and the fiber sensor 28 can therefore be configured by the minimum necessary number of sensing parts 32.

By the first to fourth deciding methods described above, the number of the anticipated inflection points can be decided so that the space between the anticipated inflection points may not be unnecessarily extremely small. When two anticipated inflection points are decided as in FIG. 8, three or more sensing parts 32 are provided.

As described above, the anticipated inflection points which are the points at both ends of the range in which a little change of the bending amount can be expected are decided in the shape of the insertion section 16, and the bending amount can be accurately detected by the minimum number of detection points in actual use.

Figure 8:
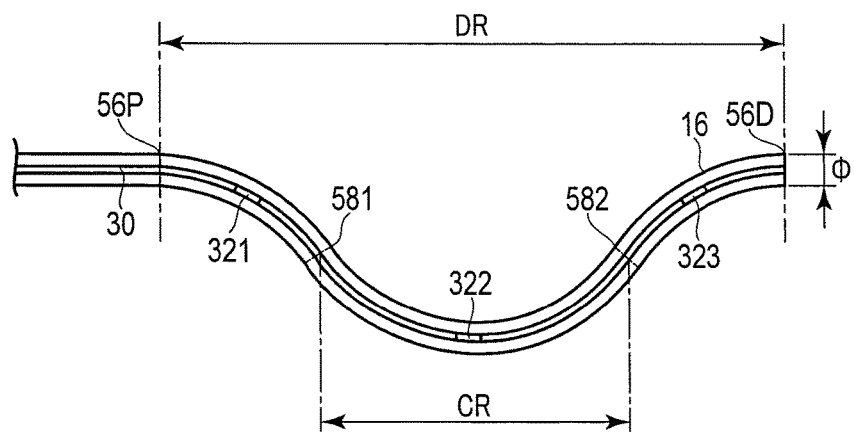
FIG. 8 is a diagram illustrating deciding methods of the number of sensing parts of the fiber sensor according to the first embodiment.

Furthermore, the sensing part 32 is preferably located in the vicinity of the midpoint between the anticipated inflection points (the first anticipated inflection point 581 and the second anticipated inflection point 582 in FIG. 8) adjacent in the longitudinal direction of the insertion section 16. Alternatively, there is a case where no anticipated inflection points are set, for example, at the ends of the insertion section 16, in which case the sensing part 32 is preferably located in the vicinity of the midpoint between the end of the insertion section 16 and the anticipated inflection point. In addition, the end of the insertion section 16 here signifies the end within the detection target range DR that is a range in which the bending state is detected by the fiber sensor 28. For example, when the end of the insertion section 16 is an unbendable rigid portion and does not require the detection of the bending state, it is possible to detect the bending state of a part of the insertion section 16 which is only a soft portion other than the rigid portion. In this case, an end within the range (detection target range DR) in which the bending state is detected is considered as the end.

Consequently, the bending amount within the range intervening between the anticipated inflection points is more easily detected, and detection accuracy of the bending amount is improved.

The shape calculation range CR is described here.

Figure 13:
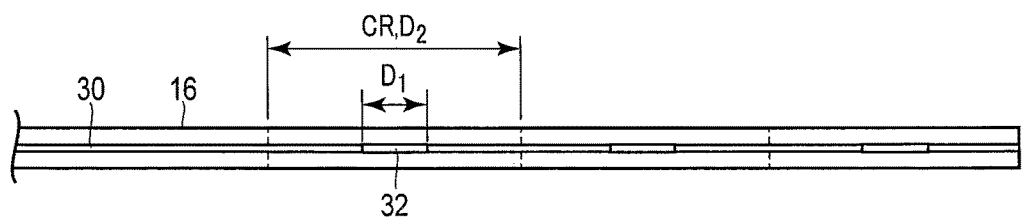
FIG. 13 is a diagram illustrating a shape calculation range.

FIG. 13 is a diagram showing the shape calculation range CR that is a range in which the operation circuit 38 calculates a shape on the basis of the state, that is, the bending amount detected with regard to the sensing part 32 of the fiber sensor 28. In general, when the shape calculation range CR is set within the range intervening between the adjacent anticipated inflection points, a shape can be accurately calculated, which is preferable.

Although the bending amount of each of the sensing parts 32 itself is detected, the sensing part 32 (e.g. having a length of 5 mm in the longitudinal direction of the fiber sensor 28) does not bend alone in actuality. Due to the structure and material of the optical fiber 30 itself or the member incorporating the fiber sensor 28, the optical fiber 30 also bends in a certain range (e.g. 60 mm) in the longitudinal direction. Therefore, it can be considered that the sensing part 32 detects the bending amount not only at the position where this sensing part 32 is present but also in a certain range (=the shape calculation range CR) of, for example, a total of 60 mm including 30 mm each in the front and rear from the sensing part in the longitudinal direction of the optical fiber 30. Here, if the length of the sensing part 32 is too small as compared to the shape calculation range CR, there is a stronger possibility that the bending amount in the shape calculation range CR may be different from the bending amount detected with regard to the sensing part 32, leading to accuracy deterioration. Thus, a length $D_1$ of the sensing part 32 in the longitudinal direction is equal to or more than ⅛ of a length $D_2$ of the shape calculation range CR of each of the sensing parts 32 that is a length by which an accurate bending amount can be detected due to the structure and material of the insertion section 16.

In normal use in which the bending state of the insertion section 16 is detected as described above, desired detection accuracy can be expected when there is the length $D_1$ of the sensing part 32 that is equal to or more than ⅛ of the length $D_2$ of the shape calculation range CR due to the structure and material of the insertion section 16. Further, the length $D_1$ of the sensing part 32 is preferably equal to or more than ½ of the length $D_2$ of the shape calculation range CR when a more accurate bending state is detected, whereas the length $D_1$ may be equal to or more than 1/30 of the length $D_2$ when a low degree of accuracy to detect a rough bending state is enough.

Thus, the sensing part 32 is configured to have a length necessary to detect the bending state in the shape calculation range CR, so that the bending amount can be accurately detected.

As described above, according to the present first embodiment, the number of the anticipated inflection points is decided, and the number of sensing parts 32 is the number of the anticipated inflection points+one or more, whereby the bending state detected in actual use can be accurately detected by the minimum number of detection points. Further, because the number of optical fibers 30 incorporated in the insertion section 16 which is the detection target can be reduced by the reduction in the number of necessary sensing parts 32, the optical fibers 30 can also be mounted in an endoscope 12 having a thin insertion section 16. Moreover, technical difficulty also decreases regarding the method which detects bending states by one optical fiber 30 because the number of sensing parts 32 in one optical fiber 30 can be reduced. Both of the methods can reduce costs.

[Modification]

Although the third deciding method described above decides the upper limited such that the number of sensing parts 32 may not be unnecessarily great, it is also possible to decide a lower limit such that the number of sensing parts 32 may not be small.

Figure 14:
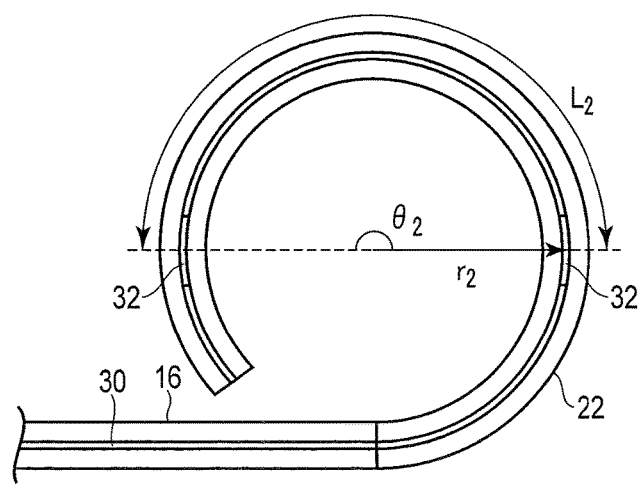
FIG. 14 is a diagram illustrating another example of the arrangement of the sensing parts of the fiber sensor in the operation bending portion of the endoscope.

As shown in FIG. 14, when the operation bending portion 22 is bent by the operation of the bending operation knob 26 provided in the operation section 18, the operation bending portion 22 is generally bent in the same direction within the range of the longitudinal direction of the operation bending portion 22, so that there are no inflection points. Thus, at least one sensing part 32 is enough because there are no inflection points in the bending by the operation of the bending operation knob 26. However, the curvature is not necessarily the same in the whole shape calculation range CR of one sensing part 32, and there is a stronger possibility of a shape having different curvatures when the shape calculation range CR is larger. Therefore, it is preferable that the shape calculation range CR is not extremely large in a range having no inflection points as well.

Thus, when $L_2$ is a space between the centers of the sensing parts 32 adjacent in the longitudinal direction, the space $L_2$ satisfies Equation (2) below:

$$L_2 = r_2 \cdot \theta_2 \qquad (2)$$

wherein $r_2$ is a curvature radius at the maximum bending of the operation bending portion 22 by the operation of the bending operation knob 26 (the bending shape of the operation bending portion 22 may vary in bending amount in the longitudinal direction to some degree, in which case $r_2$ is a curvature radius of a circle approximate to the shape of the operation bending portion 22), $\theta_2$ is a central angle of an arc created by the space between the sensing parts 32 at the maximum bending, and $\theta_2 \leq \pi$.

This can prevent the shape calculation range CR from being extremely large. That is, the number of sensing parts 32 necessary for bending amount detection are arranged in a range in which there is a stronger possibility of bending in different amounts and accurate detection is not possible by one sensing part 32, so that detection accuracy of the bending amount improves.

Although the arrangement of the sensing parts 32 in the operation bending portion 22 is described here, the sensing parts 32 may be arranged in any range of the insertion section 16. The arrangement of the sensing parts 32 can be decided by similar Equation (2) in accordance with the bending shape at the maximum bending in which the insertion section 16 can be structurally or functionally bent or can be bent in actual use, for example, when the insertion section 16 is bent by the maximum force applied to the insertion section 16 which is anticipated in actual use.

Figure 15:
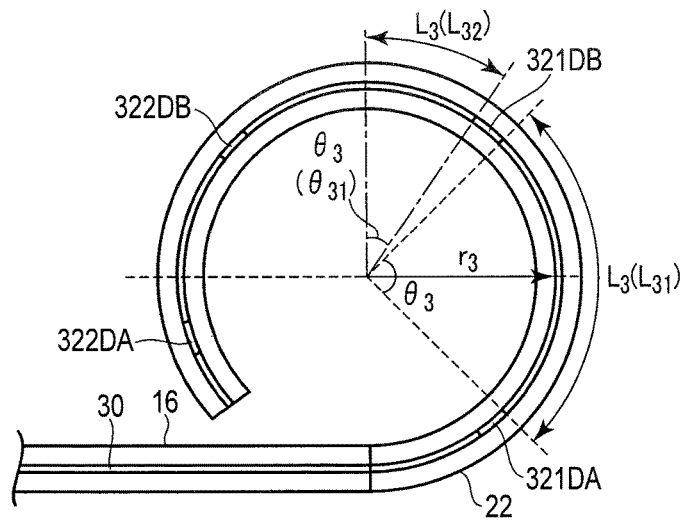
FIG. 15 is a diagram illustrating one example of the arrangement of the sensing parts of the fiber sensor in the operation bending portion of the endoscope in the case where one sensing part is divided into two and then arranged.

Furthermore, one sensing part 32 may be divided into more than one part and then arranged in the longitudinal direction of the insertion section 16. FIG. 15 is a diagram in which one sensing part 32 is divided into two divided sensing parts and then arranged. The first sensing part 321 is divided into two divided sensing parts 321DA and 321DB, and the second sensing part 322 is divided into two divided sensing parts 322DA and 322DB. The sensing part 32 more easily detects the bending of the insertion section 16 when the sensing part 32 is formed in the largest possible range in the shape calculation range CR, that is, formed long in the longitudinal direction of the insertion section 16, so that accuracy improves. On the other hand, if the sensing part 32 is longer, there is more light attenuation, so that the detection sensitivity deteriorates, and accuracy deteriorates on the other hand. Accordingly, one sensing part 32 is divided into the divided sensing parts and then arranged, so that the length of the sensing part 32 (the total length of the divided sensing parts) is not extremely great, that is, sensitivity does not deteriorate, and the sensing part 32 is widely disposed in the shape calculation range CR, leading to an improvement in detection accuracy.

Moreover, when $L_3$ is a divided sensing part space which is a space $L_{31}$ between the inner ends of the divided sensing parts 321DA and 321DB that are divided and arranged or a space $L_{32}$ between the boundary of the shape calculation range CR and the end of the divided sensing part 321DB on the side of the boundary of the shape calculation range CR, the dividing number and arrangement of the sensing part 32 are decided so that the divided sensing part space $L_3$ satisfies the equation below:

$$L_3 = r_3 \cdot \theta_3 \qquad (3)$$

wherein $r_3$ is a curvature radius at the maximum bending of the operation bending portion 22, $\theta_3$ ($\theta_{31}$, $\theta_{32}$) is a central angle of an arc created by the divided sensing part space at the maximum bending, and $\theta_3 \leq \pi/2$.

As a result, the space between the divided sensing parts is no longer extremely great, and the detection accuracy of the bending amount in the shape calculation range CR can be increased.

Figure 16:
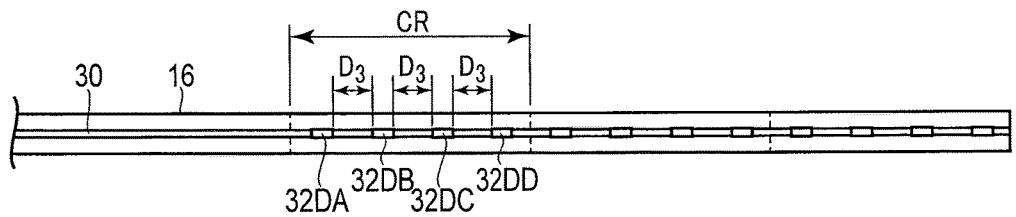
FIG. 16 is a diagram illustrating an example of the arrangement of the sensing parts of the fiber sensor in the case where one sensing part is divided into four and then equally arranged.

Furthermore, when one sensing part 32 is divided into more than one part and then arranged in the longitudinal direction of the insertion section 16, the divided sensing parts which are divided in the shape calculation range CR are preferably arranged with equal or nearly equal spaces. FIG. 16 shows a case where one sensing part 32 is divided into four divided sensing parts 32DA to 32DD that are equally arranged with a space $D_3$. When the divided sensing parts are not equally arranged, there are some parts where ranges having no divided sensing parts are wider, so that it becomes difficult to detect the change of the bending amount as a whole in the shape calculation range CR. In contrast, when the divided sensing parts 32DA to 32DD are equally arranged as above, the bending amount in the shape calculation range CR can be evenly detected, leading to an improvement in detection accuracy.

Figure 17:
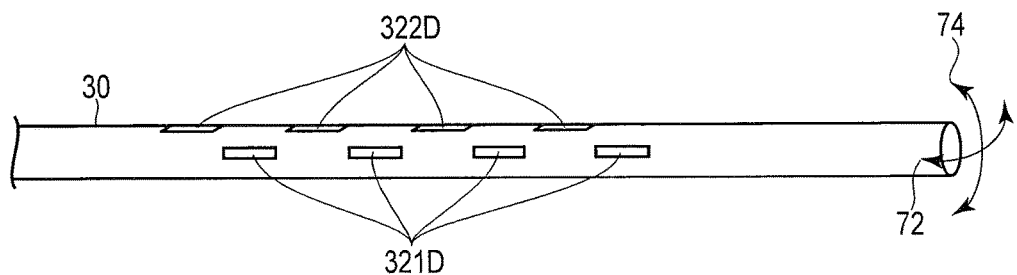
FIG. 17 is a diagram illustrating the configuration of a fiber sensor having, in the same optical fiber, a first sensing part, and a second sensing part which detects a bending amount in a direction different from that of the first sensing part.

FIG. 17 is a diagram showing the fiber sensor 28 in which the same optical fiber 30 is provided with the first sensing part 321 to detect a bending amount in a direction indicated by the reference mark 72 in the diagram, and the second sensing part 322 to detect a bending amount in a direction indicated by the reference mark 74 in the diagram different from the direction of the bending amount detected by the first sensing part 321.

In the case where bending amounts different in bending direction are detected at the same position in the longitudinal direction of the insertion section 16, the accuracy of the bending amount is higher when the positions of the sensing parts 32 in the longitudinal direction of the insertion section 16 are the same or located in the vicinity of one another as shown in FIG. 7 than when the sensing parts 32 are provided at different positions, which is therefore preferable. However, when the sensing parts 32 are provided in the same optical fiber 30, there is concern that the strength of the optical fiber 30 may deteriorate if the sensing parts 32 are provided at the same position in the longitudinal direction of the insertion section 16.

Accordingly, as shown in FIG. 17, the first and second sensing parts 321 and 322 are respectively configured as divided sensing parts 321D and 322D that are divided in the longitudinal direction of the insertion section 16, and the first divided sensing parts 321D and the second divided sensing parts 322D are arranged between one another in the longitudinal direction of the insertion section 16, that is, alternately arranged. As a result, the first and second sensing parts 32 are arranged in the vicinity of each other, and the first or second divided sensing parts 321D or 322D alone are provided at the same position in the longitudinal direction of the insertion section 16, so that accuracy is improved, and deterioration of the strength of the optical fiber 30 can also be avoided at the same time.

Although all the first and second divided sensing parts 321D and 322D are divided are alternately arranged in the example shown in FIG. 17, at least some of the first or second sensing parts 321 or 322 have only to be arranged between the other of the first or second sensing parts 321 or 322 (regarding their positions in the longitudinal direction of the insertion section 16). For example, some of the first or second sensing parts 321 or 322 may be alternately arranged, or the second divided sensing parts 322D may be arranged between the first divided sensing parts 321D.

FIG. 18 is a diagram in which one sensing part 32 is divided into two divided sensing parts 32DA and 32DB and then arranged. When the sensing part 32 is divided into more than one part in this way, a length $D_4$ between both ends is equal to or more than ⅛ of the shape calculation range CR that is a range in which the operation circuit 38 calculates a shape on the basis of the bending amount detected with regard to this sensing part 32.

Although the whole insertion section 16 is bendable in the examples described above, the number of sensing parts 32 can be decided in a similar manner when there are some rigid portions that do not bend. In this instance, the rigid portions do not change in shape, and therefore do not need to have the sensing parts 32 disposed therein.

Furthermore, the bending shape is not necessarily detected in the entire length of the insertion section 16. For example, in the insertion into the large intestine (FIG. 12), passing through the sigmoid colon is difficult, so that the shape of the anterior side of the insertion section 16 is more important than its posterior side. Therefore, the sensing parts 32 may be arranged in the detection target range DR that is, for example, only 40 cm from the distal end of the insertion section 16 so that the bending state can be detected in the sigmoid colon within the distal-side range of the insertion section 16. This leads to the reduction in the number of sensing parts 32, and still ensures that detection can be conducted at the time of the escape from the sigmoid colon where the state detection of the insertion section 16 is needed.

Second Embodiment

In the present second embodiment, an arrangement method of the sensing parts 32 in the case where the insertion section 16 has structures different in the longitudinal direction.

As the configuration of the operation bending portion 22, cylindrical first rigid members 601 and second rigid members 602 shorter than the first rigid members 601 are turnably linked by the bending mechanism 62, as shown in FIG. 19. The bending mechanism 62 turnably links the anterior and posterior rigid members 601 and 602, for example, by rivets. The curvature at the maximum bending is greater in the longitudinal range of the operation bending portion 22 composed of the second rigid members 602 than in the longitudinal range of the operation bending portion 22 composed of the first rigid members 601 because the second rigid members 602 are shorter than the first rigid members 601. The shape tends to be more complicated in the range that can have a great curvature than in the range which only allows bending with a small curvature. That is, more sensing parts 32 are needed to accurately detect the bending state having a great curvature than to detect the bending state having a small curvature. Thus, the sensing parts 32 are more densely arranged in the range composed of the second rigid members 602 than in the range composed of the first rigid members 601.

FIG. 20 shows the internal structure of the operation bending portion 22 different from that in FIG. 19, and the slits 66 are provided in the long and rigid cylindrical member 64. The slits 66 serve as the bending mechanisms 62, and the ranges intervening between the slits 66 serve as the first and second rigid members 601 and 602. The second rigid members 602 are shorter than the first rigid members 601, and the space between the slits 66 is small. In the case of such a structure as well, the sensing parts 32 are more densely arranged in the range composed of the second rigid members 602 than in the range composed of the first rigid members 601.

As described above, according to the present second embodiment, even in the structure in which the rigid members 60 of the insertion section 16 are different in length in the longitudinal direction of the insertion section 16, the sensing parts 32 are more densely arranged in the range having the short rigid portions than in the range having the long rigid portions, so that it is possible to accurately detect the bending amount without unnecessarily increasing the number of sensing parts 32.

[Modification]

Figure 21:
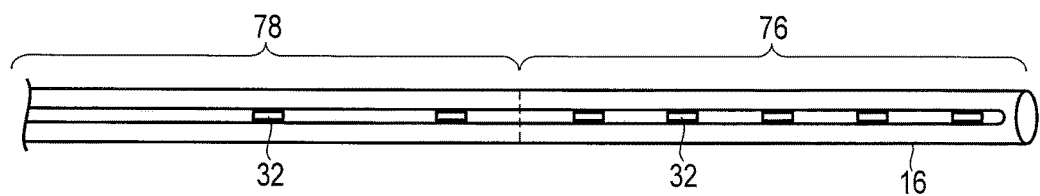
FIG. 21 is a diagram illustrating the arrangement of the sensing parts of the fiber sensor when applied to an insertion section of the endoscope having a structure which varies in hardness against bending in a longitudinal direction.

There is known an insertion section 16 having a structure in which hardness against bending varies in the longitudinal direction, as shown in FIG. 21. The insertion section 16 has a soft structure portion 76 on the distal side, and a hard structure portion 78 on the proximal side. The insertion section 16 having such a structure tends to have a shape in which the bending amount greatly varies in the longitudinal direction of the insertion section 16 in the soft range of the soft structure portion 76, so that the sensing parts 32 are more densely arranged in the soft range of the soft structure portion 76 than in the hard range of the hard structure portion 78.

Figure 22:
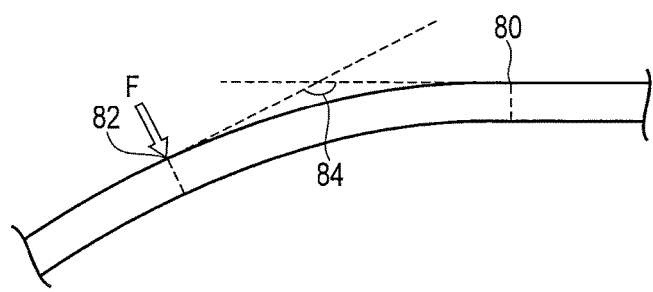
FIG. 22 is a diagram illustrating a technique to judge hardness against the bending of the insertion section.

Here, the judgment of hardness against the bending of the insertion section 16 is described with reference to FIG. 22. In the range in which hardness needs to be judged, one end is used as a supporting point 80 to support the insertion section 16. Then the other end is used as a force point 82 to apply certain force. Further, when the angle between the axis of the supporting point 80 along the longitudinal direction of the insertion section 16 and the axis of the force point 82 along the longitudinal direction of the insertion section 16 is a bending angle 84, it is judged that the range in which the bending angle 84 is small is soft and that the range in which the bending angle 84 is large is hard. In addition, when hardness is compared in different ranges, the space between the supporting point 80 and the force point 82 is constant.

In this way, hardness against the bending of the insertion section 16 can be judged. Moreover, the sensing parts 32 are more densely arranged in the soft range than in the hard range in the insertion section 16 having the structure in which hardness against bending varies in the longitudinal direction, so that it is possible to accurately detect the bending amount without unnecessarily increasing the number of sensing parts 32.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A fiber sensor comprising:
   at least one optical fiber having one or more sensing parts;
   a light emitter configured to cause light to enter the at least one optical fiber; and
   a light receiver configured to receive light emitted from the at least one optical fiber, wherein
   the at least one optical fiber is laid in a detection target at least a part of which is bendable and is arranged along a longitudinal direction of the detection target in a detection target range which is the at least the part of the detection target,
   the fiber sensor is configured to detect light guided through the at least one optical fiber and thereby detect a state of the detection target range of the detection target,
   when anticipated inflection points are inflection points of a shape of the detection target range and are anticipated from one of a possible shape of the detection target range of the detection target and a state detectable in the detection target range, the at least one optical fiber has the sensing parts whose number is the number of the anticipated inflection points+one or more,
   the number of the anticipated inflection points is decided based on one of a functional limit and a structural limit which limit a degree of freedom in a bending shape of the detection target,
   a space $L_1$ between the anticipated inflection points is $$L_1 = r_1 \cdot \theta_1$$

wherein $r_1$ is a curvature radius at a maximum bending of the detection target range of the detection target, $\theta_1$ is a central angle of an arc created by the space between the anticipated inflection points at the maximum bending, and $\theta_1 \geq \pi/2$.

2. The fiber sensor according to claim 1, wherein
   a structure of the detection target in the detection target range comprises:
   rigid members; and
   a bending mechanism which bends a range of the detection target comprising the rigid members, and
   the space between the anticipated inflection points is equal to or more than ten times the rigid member.

3. The fiber sensor according to claim 1, wherein
   the detection target has a long and tubular shape, and
   the space between the anticipated inflection points is equal to or more than ten times a diameter of the detection target in the detection target range.

4. The fiber sensor according to claim 1, wherein
   the detection target range of the detection target has an insertion section to be inserted into a subject, and
   the number of the anticipated inflection points is decided on the basis of a structure of the subject.

5. The fiber sensor according to claim 1, wherein
   the detection target in the detection target range has structures different in the longitudinal direction, and
   the sensing parts are densely or sparsely arranged on the basis of the structure of the detection target in the detection target range.

6. The fiber sensor according to claim 5, wherein
   the structure of the detection target in the detection target range comprises:
   first rigid members;
   second rigid members whose length in the longitudinal direction is smaller than that of the first rigid members;
   a first bending mechanism configured to bend a range of the detection target comprising the first rigid members; and
   a second bending mechanism configured to bend a range of the detection target comprising the second rigid members, and
   the sensing parts are more densely arranged in the range of the detection target comprising the second rigid members than in the range of the detection target comprising the first rigid members.

7. The fiber sensor according to claim 5, wherein
   the structure of the detection target in the detection target range varies in hardness against bending in the longitudinal direction, and
   the sensing parts are more densely arranged in a range of the detection target in which the hardness against bending is low than in a range of the detection target in which the hardness against bending is high.

8. The fiber sensor according to claim 7, wherein
   when certain force is applied to a force point opposite to a supporting point, the supporting point supporting at one end of a certain range in which the hardness of the detection target is judged, the force point being at the other end of the certain range, the hardness of the detection target against bending in the detection target range is judged on the basis of an angle formed by an axis along the longitudinal direction of the detection target at the supporting point and an axis along the longitudinal direction of the detection target at the force point.

9. The fiber sensor according to claim 1, wherein
the sensing parts are arranged substantially in the midpoint, in the longitudinal direction, of one of: a range intervening between the adjacent anticipated inflection points; and a range intervening between the anticipated inflection point and an end of the detection target range.

10. The fiber sensor according to claim 1, wherein
a sensing part space $L_2$ which is a space between centers of the sensing parts adjacent in the longitudinal direction of the detection target in the detection target range is $$L_2 = r_2 \cdot \theta_2$$

wherein $r_2$ is a curvature radius at the maximum bending of the detection target range of the detection target, $\theta_2$ is a central angle of an arc created by the sensing part space at the maximum bending, and $\theta_2 \leq \pi$.

11. The fiber sensor according to claim 1, wherein
at least one of the sensing parts is disposed as divided sensing parts which are divided from this one sensing part in the longitudinal direction.

12. The fiber sensor according to claim 11, wherein
the dividing number and arrangement of the divided sensing parts are decided so that a divided sensing part space $L_3$ is $$L_3 = r_3 \cdot \theta_3$$

wherein the divided sensing part space $L_3$ is one of: a space between inner ends of the divided sensing parts; and a space between an end of a shape calculation range that is a range where a shape of the detection target range of the detection target is calculated on the basis of the state detected in the divided sensing parts, and ends of the divided sensing parts on the side of the end of the shape calculation range, $r_3$ is a curvature radius at the maximum bending of the detection target range of the detection target, $\theta_3$ is a central angle of an arc created by the divided sensing part space at the maximum bending, and $\theta_3 \leq \pi/2$.

13. The fiber sensor according to claim 11, wherein
the divided sensing parts are arranged so that a space between inner ends of the adjacent divided sensing parts is substantially equal.

14. The fiber sensor according to claim 11, wherein
one of the optical fibers included in the at least one optical fiber has a first sensing part, and a second sensing part which detects a state in a direction different from that of the first sensing part,
at least one of the first and second sensing parts is configured as divided sensing parts which are divided into more than one part in the longitudinal direction, and
at least some of the divided sensing parts of the at least one of the first and second sensing parts are arranged across the other sensing part in the longitudinal direction.

15. The fiber sensor according to claim 1, wherein
a length of each of the sensing parts in the longitudinal direction is equal to or more than ⅛ of a shape calculation range that is a range where a shape of the detection target range of the detection target is calculated on the basis of the state detected in the sensing parts.

16. The fiber sensor according to claim 1, wherein
the detection target is an endoscope insertion section to observe an inner surface of a subject.

* * * * *